United States Patent
Tello et al.

(10) Patent No.: US 12,064,283 B2
(45) Date of Patent: Aug. 20, 2024

(54) METHOD FOR DETERMINING VENTRICLE CONTRACTILITY INDEPENDENTLY OF LOAD

(71) Applicant: JUSTUS-LIEBIG-UNIVERSITAET GIESSEN, Giessen (DE)

(72) Inventors: Khodr Tello, Lich (DE); Henning Gall, Heuchelheim (DE); Ardeschir Ghofrani, Wettenberg (DE); Werner Seeger, Biebertal (DE)

(73) Assignee: JUSTUS-LIEBIG-UNIVERSITAET GIESSEN, Giessen (DE)

( * ) Notice: Subject to any disclaimer, the term of this patent is extended or adjusted under 35 U.S.C. 154(b) by 0 days.

(21) Appl. No.: 17/401,024

(22) Filed: Aug. 12, 2021

(65) Prior Publication Data

US 2022/0061799 A1  Mar. 3, 2022

(30) Foreign Application Priority Data

Aug. 13, 2020 (EP) ..................................... 20190939

(51) Int. Cl.
*A61B 8/00* (2006.01)
*A61B 8/04* (2006.01)
(Continued)

(52) U.S. Cl.
CPC .................. *A61B 8/04* (2013.01); *A61B 8/06* (2013.01); *A61B 8/5207* (2013.01)

(58) Field of Classification Search
CPC ........... A61B 8/04; A61B 8/06; A61B 8/5207; A61B 5/02028; A61B 8/065; A61B 8/0883; A61B 8/485; A61B 8/5223; A61B 8/488

See application file for complete search history.

(56) References Cited

U.S. PATENT DOCUMENTS

| 6,090,047 A * | 7/2000 | Kass ....................... A61B 5/352 600/481 |
| 9,168,021 B2 * | 10/2015 | Pernot ....................... A61B 8/08 |

(Continued)

FOREIGN PATENT DOCUMENTS

DE  102013004110 A1  9/2013

OTHER PUBLICATIONS

T. Skjaerpe and L. Hatle; Noninvasive estimation of systolic pressure in the right ventricle in patients with tricuspid regurgitation; Section of Cardiology, Regional Hospital of Trondheim, Norway; European Heart Journal (1986) 7, 704-710 (Year: 1986).*

(Continued)

*Primary Examiner* — Joel Lamprecht
*Assistant Examiner* — James F McDonald, III
(74) *Attorney, Agent, or Firm* — MARSHALL, GERSTEIN & BORUN LLP

(57) ABSTRACT

A method for determining contractility independent of load Ees of a ventricle of a person is provided. The chronological profile of blood pressure during isovolumetric contraction (IVK) and isovolumetric relaxation (IVR) is first determined for a at least one ventricle over at least one period of a person's heartbeat. The at least one resulting pressure curve is then calibrated and normalized, and then the end-systolic pressure is determined from this calibrated, normalized pressure curve. The profile of blood volume over time is determined during isovolumetric contraction (IVK) and isovolumetric relaxation (IVR) for a ventricle over at least one period of a person's heartbeat, to determine the end-systolic volume Ves. The intercept VO is then determined from this end-systolic volume Ves, and contractility independent of load Ees of an examined ventricle of a person is calculated as a slope from the end-systolic pressure Pes, the end-systolic volume Ves, and the intercept V0.

4 Claims, 6 Drawing Sheets

(51) Int. Cl.
*A61B 8/06* (2006.01)
*A61B 8/08* (2006.01)

(56) References Cited

U.S. PATENT DOCUMENTS

| | | | |
|---|---|---|---|
| 10,702,247 B2* | 7/2020 | Hare, II | A61B 8/5207 |
| 2013/0245441 A1 | 9/2013 | Datta | |
| 2014/0121549 A1* | 5/2014 | Claus | A61B 8/485 |
| | | | 600/509 |
| 2016/0310103 A1* | 10/2016 | Liu | A61B 8/06 |
| 2017/0188978 A1* | 7/2017 | Kale | A61B 5/349 |

OTHER PUBLICATIONS

David A. Kass, M.D., W. Lowell Maughan, M.D., Zhong Mao Guo, M.D., Alan Kono, M.D., Kenji Sunagawa, M.D., and Kiichi Sagawa, M.D.; Comparative influence of load versus inotropic states on indexes of ventricular contractility: Circulation 76, No. 6, 1422-1436, 1987. (Year: 1987).*

François Haddad, Sharon A. Hunt, David N. Rosenthal and Daniel J. Murphy; Right Ventricular Function in Cardiovascular Disease, Part I—Anatomy, Physiology, Aging, and Functional Assessment of the Right Ventricle; Circulation. 2008;117:1436-1448 (Year: 2008).*

European Search Report for Application No. EP 20190939.7, dated Jan. 22, 2021.

Etienne Gayat et al., "Noninvasive quantification of left ventricular elastance and ventricular-arterial coupling using three-dimensional echocardiography and arterial tonometry", *American Journal of Physiology Heart and Circulatory Physiology*, vol. 301, No. 5, pp. H1916-H1923 (2011).

Chen-Huan Chen et al., "Noninvasive Single-Beat Determination of Left Ventricular End-Systolic Elastance in Humans", *Journal of the American College of Cardiology*, vol. 38, No. 7, pp. 2028-2034 (2001).

* cited by examiner

METHOD FOR DETERMINING VENTRICLE CONTRACTILITY INDEPENDENTLY OF LOAD

The invention relates to a method for determining the contractility (end-systolic elastance, Ees) of a ventricle, independently of load. The determination is made solely on the basis of ultrasonic measurements.

DESCRIPTION AND INTRODUCTION OF THE GENERAL FIELD OF THE INVENTION

Stress-independent parameters of the cardiac strength of the right ventricle are of significant importance for the characterization of patients with pulmonary diseases, in particular patients with pulmonary hypertension. Right heart function is the greatest prognostic factor in these patients.

Ultrasound cardiography (UKG), also known as heart ultrasound, supports doctors in mak-ing an accurate diagnosis of existing heart problems.

Ultrasound (sonography) works by means of sound waves. The frequency in this case is between 1 and 3 MHz. These ultrasonic waves are emitted and captured by the transducer of the ultrasound device. Different tissues reflect sound to different degrees. The information can be used to create an image of internal regions of the body in real time. Ultrasound Cardiography has Several Advantages:

The examination does not require radiation. There are no side effects from invasive surgery. Ultrasound examination is also suitable for pregnant women and patients with a contrast agent allergy. The patient can move during the treatment (compared to computed tomog-raphy or magnetic resonance imaging).

There are two ways of performing a cardiac ultrasound: the most commonly used is transthoracic echocardiography, and the less commonly used is transesophageal echocardiography.

Transthoracic echocardiography (TTE) captures the heart echo from the outside. Transthoracic echocardiography (TTE) is considered one of the standard ways to identify heart problems. The specialist places the ultrasound head on the front chest wall and can use the ultrasound image or cardiogram to identify irregularities in the coronary vessels. The method is comparable to conventional ultrasound, although there are various tech-niques that can be used to achieve precise examination results. These include:

(Color) Doppler Echocardiography:

Doppler echocardiography or color Doppler echocardiography determines the blood velocity. The function of the heart valves is verified by measuring flow velocity and detecting flow accelerations. Color-coded echocardiography makes the direction of blood flow easier to see, with red and blue colors in the cardiogram: the flow of blood towards the transducer is depicted as a red cloud, and the flow away from the transducer is depicted as a blue cloud. With this method, the doctor is able to assess whether and how the heart valves are leaking.

3D Heart Imaging:

If patients suffer from cardiac insufficiency or if the heart valves need to be examined more closely, a special probe which enables three-dimensional, i.e., spatial imaging can be used. It simplifies the assessment of heart function in real time. Thanks to its matrix transducer technology, 3D measurements are much more accurate than 2D recordings, especially since this examination technique is also able to measure the volume of the chambers and atria.

Stress Echocardiography/Exercise Echocardiography:

A load echocardiogram, often referred to as a load echo, is similar to a load ECG, but is carried out with ultrasound. The patient's body is stressed by vasodilating drugs or physical exertion. Bicycle load echocardiography is used most frequently: the patient lies on a special, tiltable echocardiography bed, and has to pedal. The load is gradually increased.

Use of contrast agent: Ultrasound contrast agents are occasionally utilized in echocardiography. This allows for, among other things, better visualizing and examination of the blood flow to the blood vessels. The contrast agent used in this case is better tolerated by patients than that used for X-rays or MRIs.

Transesophageal Echocardiography (TEE)—Swallow Echo: The transesophageal echocardiography (TEE) method is used less frequently. It is also known colloquially as a swallow echo, because a flexible tube—similar to a gastroscopy—is inserted through the mouth into the esophagus. The doctor sprays a local anesthetic into the throat to prevent any gag reflex that may arise.

There is an ultrasound probe at the tip of the tube. The advantage: the proximity of the esophagus to the heart enables clearer images (for example of the left atrium, or of possible blood clots in the case of cardiac arrhythmias). Transesophageal echocardiography also makes it easier for doctors to detect congenital heart defects.

So-called ventriculoarterial coupling represents the interplay of the ventricle and the down-stream artery, and is used, among other things, to assess the contractility or the strength of the heart in comparison to the afterload in the artery. This value is measured in both the left and right ventricles.

Ventricular arterial coupling is an approach to viewing the circulatory system as a whole. The ventricle and artery can be viewed as an elastic system in which their actions influence each other. The diastolic and systolic functions of the ventricle can supply blood to internal organs, including the ventricle itself and the distal limbs. The rules of ventricular contraction and of peripheral arterial coupling can be determined when the ventricular volume and the volume and/or pressure information of the peripheral arteries are obtained simultaneously. Among the numerous cardiac function tests, stroke volume and ejection fraction, etc., are influenced by cardiac preload, afterload, and heart rate. As such, these functional tests cannot be used to reveal the specific myocardial contractility. A wealth of data shows that the relationship between end-systolic pressure and volume plays an important role in assessing the status of systolic function. The maximum elasticity (Emax) measured by special cardiac volume catheters (so-called conductance catheters) is the slope of the ventricular end-systolic pressure/volume relationship line, which is a specific index that indicates ventricular contractility. However, due to invasiveness and high price, this cardiac catheteriza-tion is difficult to perform in a clinical setting.

Accordingly, it is necessary to provide a medical ultrasound monitoring device and method that can detect myocardial mechanical parameters in a less invasive manner.

STATE OF THE ART

Contractility independent of load cannot yet be determined by means of ultrasound examination methods, in particular for the right ventricle.

Contractility independent of load is currently determined using a pressure-volume catheter. For an example, see: Funktionsanalyse der rechten Herzkammer bei Kindern mit ange-borenen Herzfehlern mithilfe der Conductance-Technik Journal für Kardiologie—(Apitz C et al., Austrian Journal of Cardiology 2009; 16 (7-8): 264-269).

This method has been clinically tested and can be used reliably, and is also the gold standard. However, it also has disadvantages in its application. The cost for a single catheter is significant. Furthermore, the catheter is used invasively, which is very stressful for a patient.

Object

The object of the present invention is to avoid the disadvantages of the prior art, such that ultrasound examination methods can be used to determine contractility independent of load Ees. In this way, a precise and reliable diagnosis can be carried out non-invasively on the patient.

Solution of the Problem

These objects are addressed by the features of the main claim. Furthermore, advantageous configurations and developments of the invention can be found in the dependent claims.

This method can be carried out for both the right and the left ventricle. This method is par-ticularly valuable for the right ventricle, because a complete, non-invasive contractility measurement is possible. The measurement can be done entirely by means of ultrasound. Due to the difficulty of the measurement in the gold standard, the detection of contractility has so far failed. Functional analysis of the right ventricle has always been a challenge because of its complex geometry. While the shape of the left ventricle resembles an ellip-soid, the right ventricle has a crescent moon-like shape when viewed from the side, and from the anterior it appears to be approximately triangular. As a result, measurement methods previously used for the left ventricle cannot easily be transferred to the right ventricle.

The end-systolic pressure-volume relationship (elastance) is used as a measure of the contractility of a ventricle in the context of the method according to the invention. Investigations on the left ventricle have shown that there is a close relationship between the end-systolic pressure-volume relationship and the force-length relationship of an individual cardiac muscle cell or an individual papillary muscle fiber. Because the maximum force generated by a cardiac muscle cell of a given length is representative of its contractile function, it is gener-ally accepted that the end-systolic pressure-volume relationship is the most reliable representation of the mechanical contractile performance of the myocardium that can be obtained in vivo, i.e., in the intact circulation.

First, some of the terms necessary to understand the method according to the invention will be briefly explained.

Isovolumetric contraction (IVK): The ventricles contract, causing internal pressure to rise. This leads to the immediate closure of the atrioventricular (AV) valves, i.e., the mitral and tricuspid valves. The valves close because the ventricular pressure exceeds atrial pressure. This prevents blood from flowing back into the atrium. At this point all 4 heart valves are closed—that is, the pressure in the ventricles increases while the volume remains the same. This phase is the isovolumetric contraction.

Isovolumetric relaxation (IVR): When the contraction of the ventricles subsides and the internal pressure drops below the aortic pressure, the semilunar valves close again. Since all 4 heart valves are closed at this point and the volume in the ventricle does not change, this phase is referred to as isovolumetric, analogously to the stressed phase. During the relaxation phase, ventricular pressure drops rapidly. This phase is also called isovolumetric relaxation.

Regurgitation flow: Regurgitation flow is the term used to describe the flow of blood back through a heart valve.

End-systolic pressure (Pes): End-systolic pressure is the pressure that prevails in one of the two heart ventricles at the end of the heart's contraction period (systole). Pes is the pressure point at which the volume has its lowest value. The maximum right ventricular pressure Pmax is the maximum possible end-systolic pressure Pes in the right ventricle.

End-systolic volume (Ves): The end-systolic volume is the volume of blood that is present in a ventricle at the end of the systole after a ventricle has been emptied to the maximum, i.e., after the ventricle has completely contracted.

Pulmonary artery systolic pressure (sPAP): Pulmonary artery systolic pressure is the blood pressure in the pulmonary artery while the heart is contracting (systole).

The method according to the invention comprises the following steps.

Ia) Determining the chronological profile of blood pressure during isovolumetric contraction (IVK) and isovolumetric relaxation (IVR) for at least one ventricle for at least one period of a person's heartbeat.

The chronological profile of blood pressure during IVK and IVR is first determined for at least one ventricle. A pressure curve is generated for each measurement of the pressure profile over a period of one heartbeat. The determination is preferably carried out by means of cardiac sonography. An ensemble of such pressure curves is shown by way of example in FIG. 1a.

Ib) Determining the velocity (v) of the regurgitation flow past the tricuspid valve from at least one pressure curve of isovolumetric contraction (IVK) and isovolumetric relaxation (IVR) determined in step Ia)

The regurgitation flow can be determined, for example, using a Doppler flow rate measurement.

Ic) Calculating the maximum right ventricular pressure (Pmax) from the velocity (v) of the regurgitation flow from step Ib). This calculation is a routine method of heart ultrasound measurement. The Bernoulli equation is used to estimate the pressure from the velocity. Specifically: $Pmax \sim (4v)^2$. The maximum right ventricular pressure Pmax is used in the following steps to individually calibrate the pressure/time curve as a function of pressure.

Id) Calibrating the at least one pressure curve from step Ia) using the IVR and IVK times from step Ia), and the maximum right ventricular pressure (Pmax) from step Ic) of the person being examined, in order to obtain a calibrated pressure curve for this person. For the calibration, the at least one measured pressure curve is compared with pressure curves obtained from reference measurements, and is adapted in such a way that the deviations of the mean curve shape from a reference curve shape over a period of one heartbeat is minimal. The reference measurements are preferably measurements taken with a routine right heart catheter.

Ie) Normalizing at least one pressure curve from step Id) of the ventricle being examined in order to obtain a calibrated normalized pressure curve. The IVR and IVK times from step Ia), and at least one pressure curve obtained during the method, are used for the normalization in step Ie). "Normalization" in this case means the scaling of the range of values for blood pressure and time to a specific range, between 0 and 1. The normalization serves to make the results comparable with different ba-ses. At least one pressure curve is normalized using the IVR and IVK times from step Ia) and the maximum right ventricular pressure Pmax from step Ic) of the person, in order to obtain a normalized pressure curve for the specific person. An ensemble of such calibrated pressure curves is shown by way of example in FIG. 1b. The at least one pressure curve is normalized in each case by combining the measurements over one period of one heartbeat, and using the time period of the heart contraction in the following three steps:

Ie$_a$) First, the times of opening and closing of the mitral and aortic valves are assigned to the given pressure trace, using the measurement data from step Ia.

Ie$_b$) Next, the at least one pressure curve is stretched or compressed along the time axis between the time points from step Iea), such that the valve events coincide for all pressure curves.

Ie$_c$) Subsequently, the at least one time-expanded or time-compressed pressure curves from step Ie$_b$) are scaled vertically in order to obtain the same maximum right ventricular pressure Pmax. An averaged waveform is then calculated.

The maximum right ventricular pressure Pmax is used to scale the am-plitude of the pressure curve.

Optionally, after the calibration, an averaging over all calibrated normalized pressure curves is carried out. This is shown by way of example in FIG. 1c.

II. Determining the end-systolic pressure (Pes) from the at least one calibrated normalized pressure curve from step Ie). This is shown by way of example in FIG. 1d.

III. Determining the chronological profile of blood volume during the isovolumetric contraction (IVK) and the isovolumetric relaxation (IVR) for at least one ventricle over at least one period of one heartbeat of a person, wherein a volume curve is generated for each measurement of the volume profile over a period of one heartbeat. The determination is preferably carried out by means of cardiac sonography. This is shown by way of example in FIG. 2.

IV. Determining the end-systolic volume Ves from at least one volume curve from step III V. Determining the intercept V0 from the end-systolic volume Ves from step IV. The following is suitable as a good approximation: V0=−50.01 ml+0.7*Ves. This formula was determined empirically from direct measurements of V0. The gold standard method was used, which uses the so-called multi-beat method to re-duce the preload, which was achieved by briefly closing the inferior vena cava. The slope of the end-systolic pressure per volume is the contractility (end-systolic elastance), and intersects the x-axis (volume) at point V0. V0 has a linear relationship to the end-systolic volume. The above formula for V0 is the result of this linear relationship. The intercept V0 is the x-axis portion of the ventricular end-systolic pressure-volume relationship line. This is shown by way of example in FIG. 2.

VI. Determining contractility independent of load Ees of the ventricle being examined as a slope from the end-systolic pressure Pes from step II and the intercept V0 from step V. Contractility independent of load is the slope of the volume curve between the intercept V0 and the end-systolic pressure Pes. Therefore, Ees=Pes/(Ves-V0)

In a further development of the invention, it is possible to carry out the method according to the invention with an ultrasound monitoring device 1.

This device comprises several elements:

Ultrasound Measuring Element 10

The ultrasound measuring element 10 (for example an ultrasonic probe) can be attached to a body surface of a patient being examined, and is designed in such a way that it can scan the body surface and acquire an echo signal.

Alternatively, the ultrasound measuring element 10 can be introduced into the patient and is designed in such a way that an echo signal can be detected inside the body. This is the case, for example, with transesophageal echocardiography (TEE). In this case, the ultrasound examination of the heart is carried out from inside the esophagus. For the patient, the examination is similar to a gastroscopy.

In a further development of the ultrasound monitoring device 1, it includes a plurality of ultrasound probes which can be attached to the patient's ventricle, aorta and peripheral arteries to perform real-time synchronized scanning.

Blood Pressure Measuring Element 20

The blood pressure measuring element 20 is designed in such a way that it can measure at least one blood pressure parameter of a patient being examined. Blood pressure parameters can preferably be: blood pressure, peripheral arterial pulse wave information, systolic pressure, diastolic pressure, and mean arterial pressure. That blood pressure measuring element 20 is preferably an aneroid blood pressure measuring device or a finger blood pressure measuring device.

Processing Element 30

The processing element 30 is designed in such a way that it can receive an echo signal of the ultrasound measuring elements 10 and can calculate at least one blood flow parameter from the echo signal. Furthermore, it is designed in such a way that it can calculate at least one myocardial mechanical parameter (e.g. contractility independent of load) from at least one blood flow parameter and at least one blood pressure parameter.

Myocardial mechanical parameters can preferably be: the x-axis intercept of the ventricular end-systolic pressure-volume relationship line Vo, and contractility independent of load Ees. Blood flow parameters can preferably be: aortic forward Doppler blood flow signals, 2D and peripheral arterial Doppler flow signal for determining the regurgitation flow.

Furthermore, this processing element 30 is designed in such a way that it can display the blood pressure, at least one blood flow parameter, and at least one myocardial mechanical parameter, and can forward it to a display element 40.

In a further development of the ultrasound monitoring device 1, the processing element 30 is designed in such a way that it can process the echo signal digitally into a digital processing signal in order to obtain a numerical parameter, waveform, or trend graph calculation according to the digital processing signal, the digital processing signal being selected from the group consisting of: RF signal, baseband signal and envelope signal.

Display Element 40

The display element 40 is designed in such a way that it can receive and display the blood pressure, at least one blood flow parameter, and at least one myocardial mechanical parameter of the processing element 30.

Furthermore, it is possible that embodiments of the invention can be implemented in hard-ware, firmware, software, or any combination thereof.

Developments of the invention can also be implemented as instructions that are stored on a computer-readable storage medium that can be read and executed by one or more pro-cessors.

The computer-readable storage medium may include magnetic disk storage media, optical storage media, read only memory (ROM), random access memory (RAM), and the like.

In the present context, when an element (10, 20, 30, 40) is referred to as "connected" or "coupled" to another element, it may be connected or coupled directly to the other element, or there may be other elements present in-between.

EMBODIMENTS

FIG. 3 shows measurement data for a patient, by way of example. FIG. 3a shows an averaged, calibrated normalized pressure curve as obtained after step I. The right ventricle was used in this case for the measurement.

FIG. 3b shows the pressure-volume curve of the patient. The pressure-volume curve combines the profile of the determination of the chronological profile of the blood pressure from step I and of the blood volume from step III.

The echocardiography data produce the following values:

| Start of the IVK | End of the IVK | Start of the IVR | End of the IVR | sPAP |
|---|---|---|---|---|
| 0 s | 40 s | 327 s | 384 s | 90 mmHg |

The pulmonary arterial pressure sPAP corresponds to the end-systolic pressure Pes and, as described in step II, was determined from the averaged, calibrated normalized pressure curve.

The determination of the end-systolic volume Ves in step IV produced a value of 225 ml.

This value was taken from the volume curve in FIG. 3b. Step V was then carried out to determine the intercept V0. In this case, the following is used: V0=−50.01+0.7*Ves As such, the intercept is V0=107.49 ml Step VI was thus carried out to determine contractility independent of load Ees.

For contractility independent of load, the following is used: Ees=Pes/(Ves−V0)

Ees=90 mmHg/(225−107.49) ml

Consequently, the contractility independent of load is 0.77 mmHg/ml.

FIGURE LEGENDS AND LIST OF REFERENCE SYMBOLS

FIG. 1 shows, in the partial FIG. 1a), measured values of a measurement for the chronological profile of the blood pressure over the duration of one heartbeat period, by way of example. Partial FIG. 1b shows the normalized profiles of the blood pressure. Partial FIG. 1c shows the average profile of the blood pressure. Partial FIG. 1d shows the values for the blood pressure and time after the conversion from normalized units into regular units.

Figure 1A:
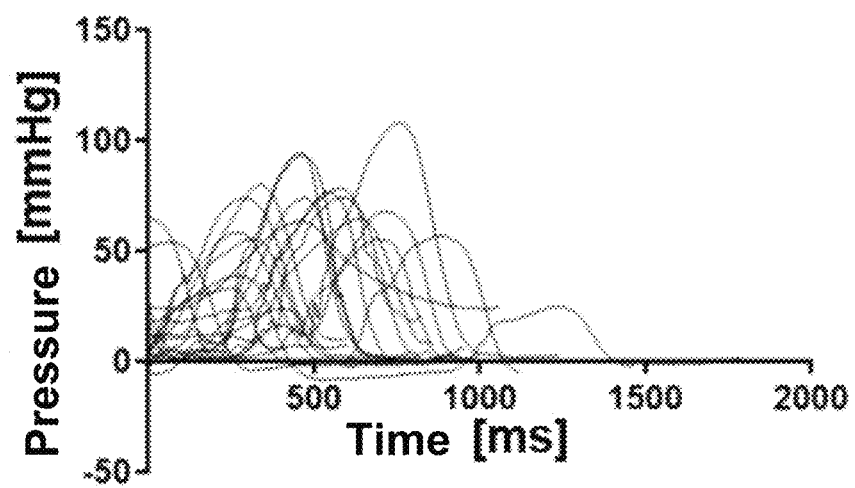
Figure 1B:
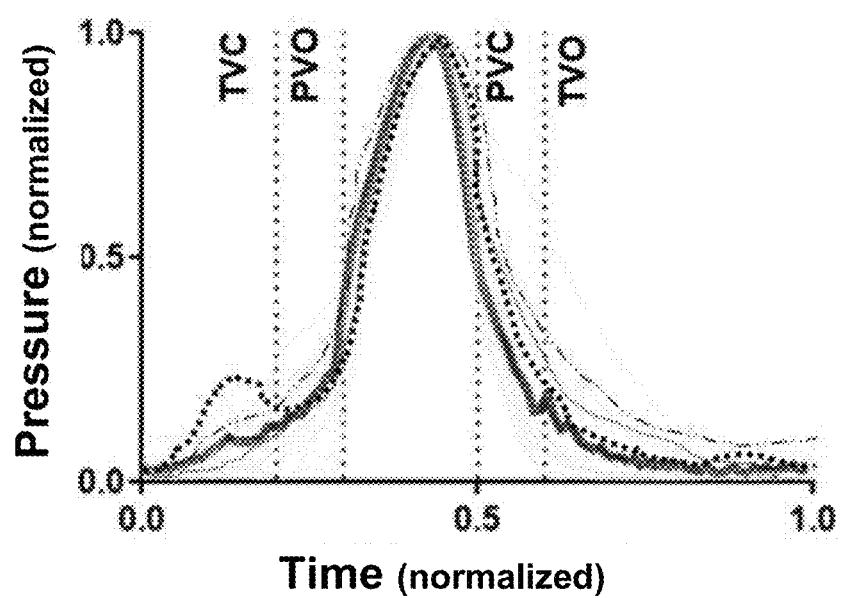
Figure 1C:
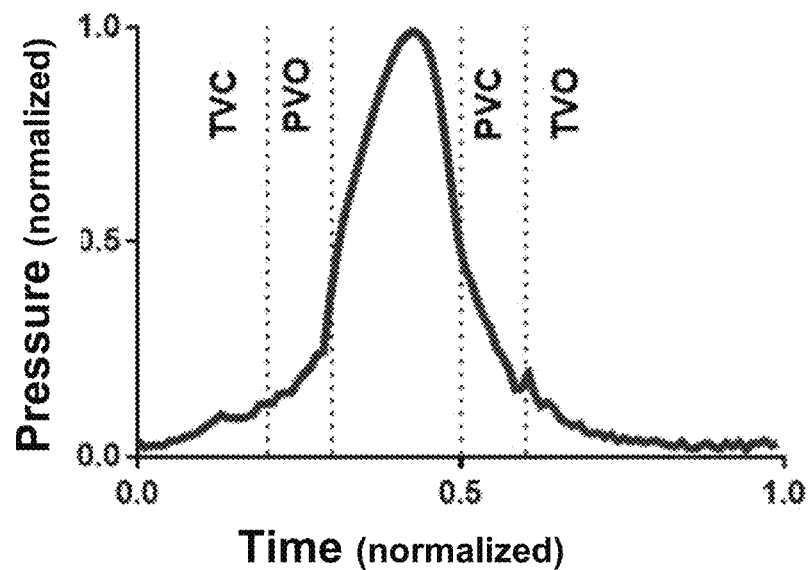
Figure 1D:
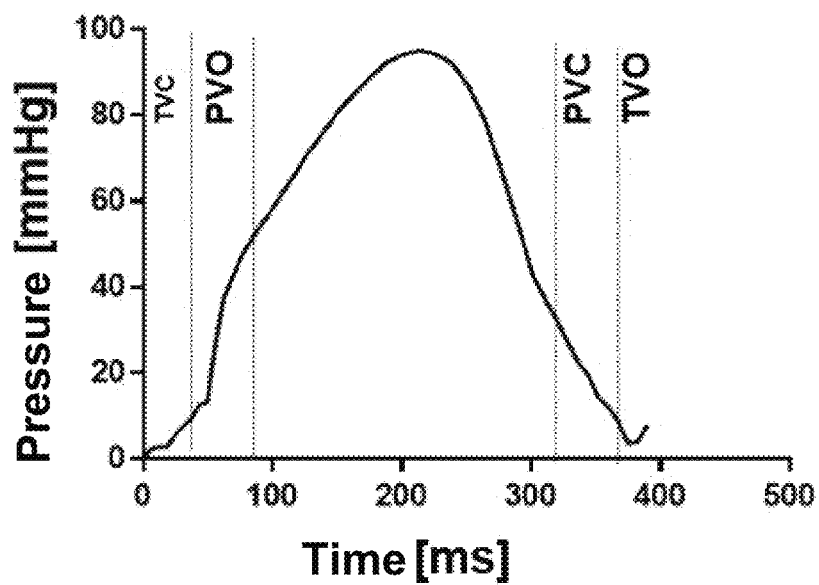
Figure 2:
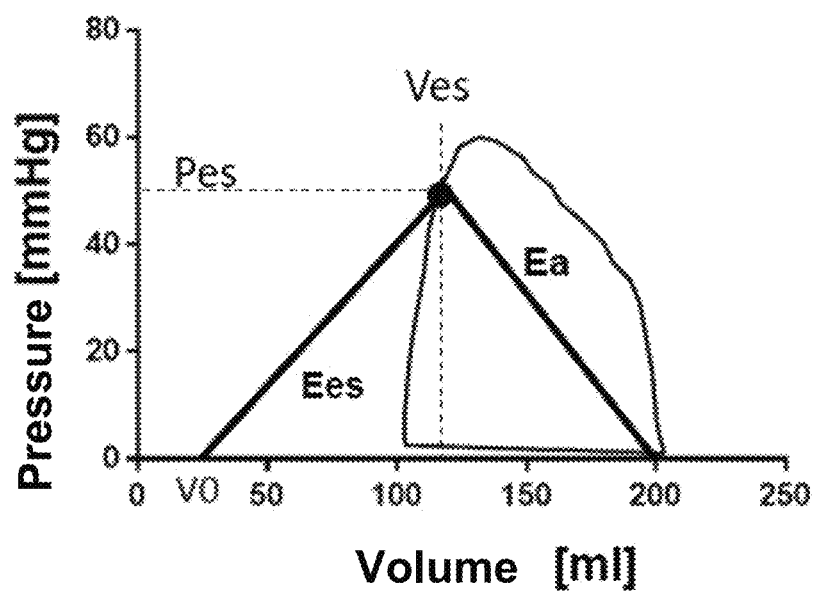
FIG. 2 shows the end-systolic volume Ves as a function of the end-systolic pressure Pes, by way of example. The volume was determined in this case by means of ultrasound measurements.
Figure 3A:
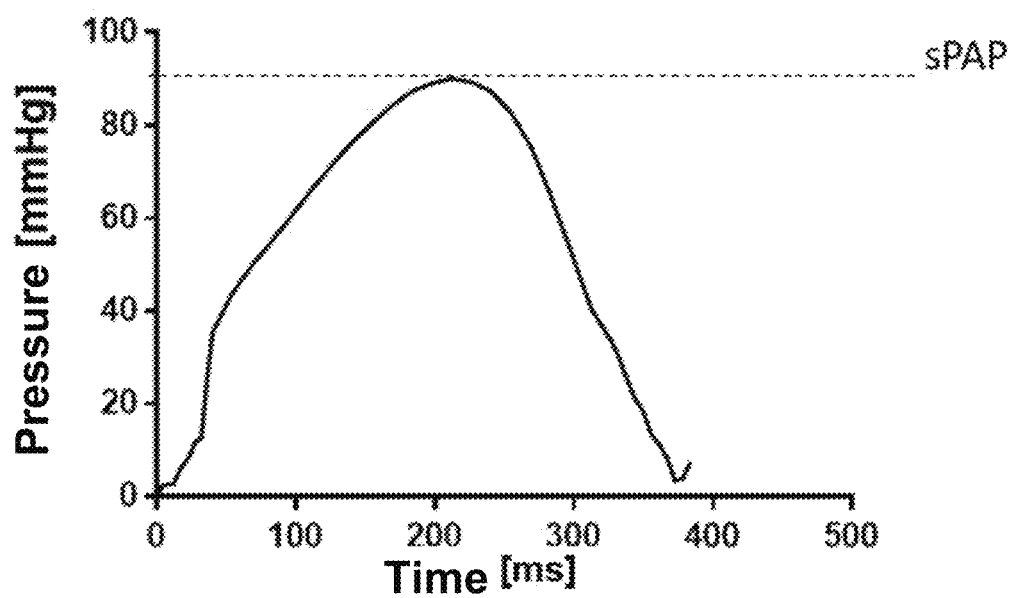
FIGS. 3A and 3B show the measured values of a sample patient.
Figure 3B:
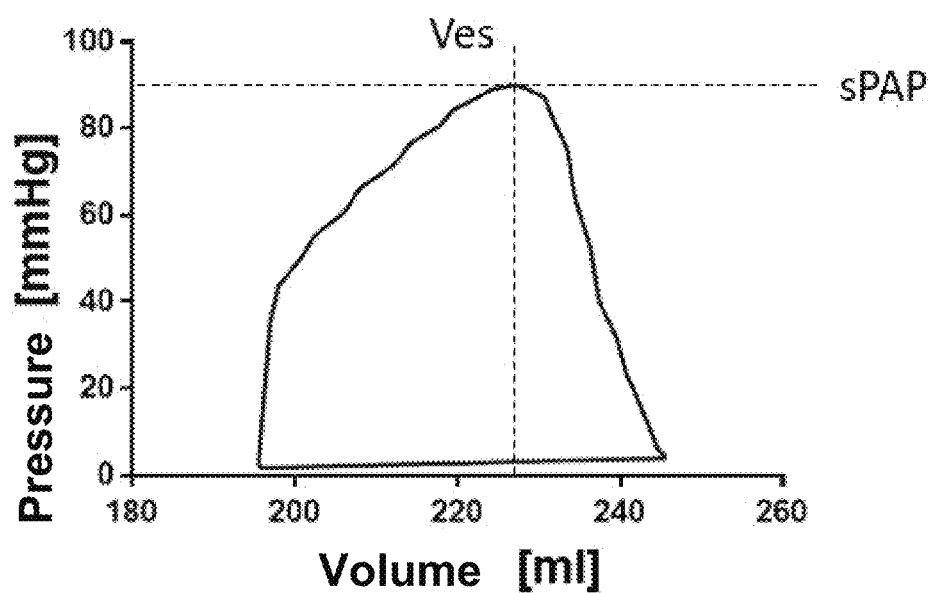

LIST OF REFERENCE SYMBOLS 1 ultrasound monitoring device
10 ultrasound measuring element
20 blood pressure measuring element
30 processing element
40 display element
TVC: tricuspidal valve closure
TVO: tricuspidal valve opening
PVC: pulmonary valve closure
PVO: pulmonary valve opening

The invention claimed is:

1. A method for non-invasively determining contractility independent of load (Ees) for at least one ventricle of a person being examined, comprising the steps of:

Ia) determining the chronological profile of a blood pressure during the isovolumetric contraction (IVK) and the isovolumetric relaxation (IVR) of the at least one ventricle by taking a plurality of blood pressure measurements over at least one period of one heartbeat of the person, wherein a plurality of pressure curves are generated corresponding to each measurement of the blood pressure profile, and wherein the blood pressure is measured by a blood pressure measuring device, Ib) determining, by a processing element, the velocity (v) of the regurgitation flow through the tricuspid valve from at least one of the plurality of pressure curves from step Ia), Ic) calculating, by the processing element, the maximum right ventricular pressure (Pmax) from the velocity (v) of the regurgitation flow from step Ib), Id) obtaining a calibrated pressure curve by calibrating at least one of the plurality of pressure curves from step Ia) using the IVR and IVK times from step Ia) and the maximum right ventricular pressure (Pmax), Ie) obtaining a calibrated normalized pressure curve by normalizing the at least one calibrated pressure curve from step Id), II. determining the profile of the blood volume over time during isovolumetric contraction (IVK) and isovolumetric relaxation (IVR) of the at least one ventricle by taking a plurality of blood volume measurements over the at least one period of one heartbeat of the person, wherein a plurality of volume curves are generated corresponding to each measurement of the volume profile, III. determining the end-systolic volume (Ves) from the at least one of the plurality of volume curves from step II, and determining the end-systolic pressure (Pes) from the at least one of the plurality of pressure curves from step I, IV. determining the intercept (V0) wherein V0=−50.01 ml+0.7*Ves from the end-systolic volume (Ves) from step III, V. determining contractility independent of load (Ees) of the ventricle being examined based on the end-systolic pressure (Pes) from step III, the end-systolic volume (Ves) from step III, and the intercept (V0) from step IV, wherein contractility independent of load (Ees) of the ventricle is the slope of the volume curve between the intercept (V0) and the end-systolic pressure (Pes), and Ees=Pes/(Ves−V0).

2. An ultrasound monitoring device for performing a method according to claim 1, comprising:

an ultrasonic probe configured to (i) attach to the person being examined or be introduced into the person, and (ii) scan a body surface and detect an echo signal, a blood pressure measuring device configured to measure at least one blood pressure parameter of the person being examined, a processing element configured to (i) receive the echo signal from the ultrasonic probe, (ii) convert the echo signal into at least one blood flow parameter, and (iii) calculate at least one myocardial mechanical parameter from the at least one blood flow parameter and the at least one blood pressure parameter, and a display element configured to receive and display the blood pressure, the at least one blood flow parameter, and the at least one myocardial mechanical parameter.

3. The method of claim 1, wherein an ultrasonic probe is used to scan a body surface of the person and detect an echo signal.

4. The method of claim 3, wherein real time 3D echocardiography is carried out to assess volume over time during step II.

* * * * *